US008703725B2

(12) United States Patent
Troup et al.

(10) Patent No.: US 8,703,725 B2
(45) Date of Patent: Apr. 22, 2014

(54) NUTRITIONAL COMPOSITIONS (71) Applicant: NESTEC S.A., Vevey (CH)

(72) Inventors: John P. Troup, Gig Harbor, WA (US); Robert R. Wolfe, League City, TX (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/687,796

(22) Filed: Nov. 28, 2012

(65) Prior Publication Data

US 2013/0090297 A1 Apr. 11, 2013

Related U.S. Application Data (63) Continuation of application No. 10/662,678, filed on Sep. 15, 2003, now abandoned.

(60) Provisional application No. 60/412,370, filed on Sep. 20, 2002, provisional application No. 60/417,203, filed on Oct. 9, 2002, provisional application No. 60/455,921, filed on Mar. 19, 2003.

(51) Int. Cl.
*A23L 1/29* (2006.01)
*A61K 31/195* (2006.01)
*A61K 31/405* (2006.01)
*A23L 2/52* (2006.01)
*A23L 1/30* (2006.01)
*A23L 1/305* (2006.01)

(52) U.S. Cl.
CPC .............. *A23L 1/293* (2013.01); *A23L 1/3006* (2013.01); *A23L 1/305* (2013.01); *A23L 1/3051* (2013.01); *A61K 31/195* (2013.01); *A61K 31/405* (2013.01); *A61K 2300/00* (2013.01); *A23L 2/52* (2013.01)
USPC ............. 514/34; 514/274; 514/249; 514/410; 514/589

(58) Field of Classification Search
CPC ....... A23L 1/293; A23L 1/296; A23L 1/3006; A23L 1/305; A23L 1/3051; A61K 31/195; A61K 31/405; A61K 2300/00
USPC ............................ 514/34, 274, 249, 410, 589
See application file for complete search history.

(56) References Cited

U.S. PATENT DOCUMENTS

| 4,112,123 A * | 9/1978 | Roberts ........................ 426/72 |
| 4,544,568 A | 10/1985 | Heyland et al. |
| 4,780,475 A | 10/1988 | Cerra et al. |
| 4,898,879 A | 2/1990 | Madsen et al. |
| 4,906,664 A | 3/1990 | Bistrian et al. |
| 5,514,656 A | 5/1996 | Cope et al. |
| 5,547,927 A | 8/1996 | Cope et al. |
| 5,576,351 A | 11/1996 | Yoshimura et al. |
| 5,700,782 A | 12/1997 | Cope et al. |
| 5,817,695 A | 10/1998 | Pelico |
| 5,827,896 A | 10/1998 | Ostlund et al. |
| 5,985,339 A | 11/1999 | Kamarei |
| 6,077,828 A * | 6/2000 | Abbruzzese et al. .......... 514/5.5 |
| 6,203,820 B1 * | 3/2001 | Vickery ........................ 424/646 |
| 6,232,346 B1 | 5/2001 | Sole et al. |
| 6,245,379 B1 | 6/2001 | Lepine |
| 6,326,355 B1 | 12/2001 | Abbruzzese et al. |
| 6,387,883 B1 | 5/2002 | Abbruzzese et al. |
| 6,420,342 B1 * | 7/2002 | Hageman et al. ............... 514/23 |
| 6,953,679 B2 * | 10/2005 | Salvati et al. ................. 435/121 |
| 2003/0119888 A1 * | 6/2003 | Allen ............................ 514/380 |

FOREIGN PATENT DOCUMENTS

| JP | 11246435 | 9/1999 |
| WO | WO89/08709 | 9/1989 |
| WO | WO97/13415 | 4/1997 |
| WO | WO98/18751 | 5/1998 |
| WO | WO98/43617 | 10/1998 |
| WO | WO99/40183 | 8/1999 |
| WO | WO00/21554 | 4/2000 |
| WO | WO02/087562 | 11/2002 |

OTHER PUBLICATIONS

Pillips Bill, Sports Supplemental Review, 1997, pp. 66-70.*
Definition of International Unit from http: //www.medterms.com/script/main/art.asp?articlekey=9650, pp. 1-3. Accessed Jun. 30, 2009.
Fryburg DA. Jahn LA, Hill Sa, Oliveras DM, Barrett EJ, Insulin and Insulin-Like Growth Factor-I Enhance Human Skeletal Muscle Protein Anabolism during Hyperaminoacidemia by Different Mechanisms, J. Clin. Invest., 1995, 96: 1722-1729.
Mantovani G. Maccio A. Massa E. Mededdu C. Managin Cancer-Related Anorxia/Cachexia, Drugs 2001, 61(4), 499-514.
Derwent Abstracts—90/020255, "Anti-cancer pharmaceutical compsns. -contain L-leucina, L-isoleucine, L-valine, L-lysine, L-threonine, L-tryptophan, L-methionine, L-cystein", Dec. 5, 1989 (1989), (XP-002099910).
Ventrucci et al., "Effect of a leucine-supplemented diet on body composition changes in pregnant rats bearing Walker 256 tumor", Braz, J. Med. Biol. Res., vol. 34, No. 3, pp. 333-338, (2001).
Beck et al., "Anticachectic and Antitumor Effect of Eicosapentaenoic Acid and Its Effect on Protein Turnover", Cancer Research, vol. 51, pp. 6089-6093, (Nov. 15, 1991).

* cited by examiner

*Primary Examiner* — Julie Ha
(74) *Attorney, Agent, or Firm* — K&L Gates LLP (57) ABSTRACT

The present disclosure is directed to compositions for the promotion of muscle protein synthesis and control of tumor-induced weight loss in patients that are, for example, suffering from cancer cachexia. The present disclosure is also directed to methods of administering such compositions.

18 Claims, 3 Drawing Sheets

NUTRITIONAL COMPOSITIONS

CROSS REFERENCE TO RELATED APPLICATIONS

The present application is continuation application of U.S. Ser. No. 10/662,678, filed Sep. 15, 2003, which claims the benefit of U.S. Provisional Application No. 60/412,370, filed Sep. 20, 2002; U.S. Provisional Application No. 60/417,203, filed Oct. 9, 2002; and U.S. Provisional Application No. 60/455,921 filed Mar. 19, 2003, the entire contents of which are being incorporated herein by reference.

BACKGROUND

Disclosed are methods and nutritional compositions for the promotion of muscle protein synthesis or the control of tumor-induced weight loss, such as cancer cachexia.

Cachexia is a condition of severe malnutrition and negative nitrogen balance characterized by anorexia (i.e. a lack or severe loss of appetite), weight loss, and muscle atrophy. The physiological, metabolic, and behavioral changes in cachexia are associated with patient complaints of weakness, fatigue, gastrointestinal distress, sleep/wake disturbances, pain, listlessness, shortness of breath, lethargy, depression, malaise and the fear of being burdensome on family and friends. Although cachexia has been classically associated with chronic infections and malignant conditions, it has also been identified in patients after extensive traumatic injury and sepsis and in aging persons with failure to thrive syndrome.

Loss of lean body mass associated with cancer cachexia not only weakens the individual and makes activities of daily living difficult, but can weaken the patient to the point that they do not have the strength to undergo chemo- and/or radiation therapy.

Two main components contribute to cancer cachexia—a loss of appetite and a metabolic response to stress that causes a preferential loss of muscle at a rate greater than would be expected from the lack of nutritional intake alone. Consequently, a nutritional supplement to ameliorate the rate of loss of muscle mass in patients with cancer would have an important clinical impact.

SUMMARY

The inventors have found that when dietary intake is limited below the optimal level for physiological or patho-physiological reasons, a dietary supplement must be more effective than normal food intake in order to provide a benefit. This is because in this circumstance, when a dietary supplement is given, normal food intake is likely to be reduced by a calorically equivalent amount. Consequently, a supplement designed to limit cancer cachexia should stimulate muscle protein synthesis to a greater extent than normal food intake and should not interfere with the response to meal intake.

Trials of conventional nutritional supplements in patients with cancer cachexia have failed to show appreciable benefit in terms of weight gain or quality of life. Accordingly, there is an urgent need for effective nutritional approaches capable of treating, preventing or ameliorating the effects of tumor-induced weight loss due to, for example, cancer cachexia and/or anorexia.

The inventors have now found that a formulation containing free essential amino acids, rather than intact protein, is optimal. In particular, and unexpectedly, the inventors have found that nutritional compositions comprising a mixture of essential amino acids in free form and/or in salt form, rather than intact protein, which mixture comprises particularly high amounts of leucine effectively stimulate muscle protein synthesis.

The compositions of the present invention, e.g. in the form of dietary means, e.g. supplements, or nutritional or pharmaceutical formulations, for the treatment or prevention of cachexia, e.g. cancer cachexia and/or anorexia can be self-administered for extensive periods without risk of adverse side-effects, yet have the potential to reverse cachexia, e.g. cancer cachexia, and/or improve associated symptoms that affect quality of life. The compositions as described herein have excellent taste and thus have particularly good patient compliance and patient acceptance due to their increased ease of administration and ingestion.

Additional features and advantages are described herein, and will be apparent from the following Detailed Description and the figures.

DETAILED DESCRIPTION

In one aspect of the present invention there is provided a composition comprising at least one of isoleucine, leucine, lysine, methionine, phenylalanine, threonine, tryptophan, valine, or histidine, e.g. leucine and at least one of isoleucine, lysine, methionine, phenylalanine, threonine, tryptophan, valine, or histidine, in free form and/or in salt form, e.g. pharmaceutically or nutritionally acceptable salt form, wherein leucine is present in an amount of at least about 10 to about 95%, e.g. about 10 to about 60%, e.g. at least about 15, 20, 25, 30 or 35% to about 40, 45, 50 or 55%, based on the weight of amino-nitrogen source, hereinafter referred to as compositions of the invention.

The term "amino-nitrogen source" as used herein refers to amino acids, e.g. essential amino acids, conditionally essential amino acids or non-essential amino acids, in free form or salt form, either alone or in combination with, e.g. in addition to, intact protein.

As used herein, the term "intact protein" refers to protein, e.g. hydrolyzed, e.g. partially hydrolyzed protein and to peptides, e.g. to amino acids which are not in free or salt form. According to the invention, the "intact protein" may be chosen from at least one of casein, whey protein, soy protein, collagen or wheat protein.

In one aspect there is provided a composition of the invention, wherein leucine in free and/or salt form is present in amount of at least about 10 to about 35%, e.g. about 11, 12, 13, 14 or 15 to about 20, 25 or 30%, e.g. at least about 14 or 15% by weight, based on the weight of total amino acids.

In a further aspect of the invention there is provided a composition of the invention wherein leucine is present in free form and/or salt form in an amount of at least about 20 to about 80%, e.g. about 20 to about 65%, e.g. about 25, 30 or 35% to about 40, 45, 50 or 55%, e.g. about 65% by weight, based on the weight of amino acids in free form and/or salt form.

The term "amino acids" as used herein, unless otherwise stated, refers to amino acids in free form and/or in salt form chosen from at least one of essential amino acids, e.g. isoleucine, leucine, lysine, methionine, phenylalanine, threonine, tryptophan, valine, or histidine, conditionally essential amino acids, e.g. tyrosine, cysteine, arginine, or glutamine, or non-essential amino acids, e.g. glycine, alanine, proline, serine, glutamic acid, aspartic acid, asparagines, taurine or carnitine.

In yet a further aspect there is provided a composition of the invention wherein leucine is present in free form and/or salt form in an amount of at least about 20 to about 95%, e.g. about 25, 30, 35, 40 or 45% to about 50, 55, 60, 65, 70, 75, 80, 85 or 90%, e.g. about 95% by weight, based on the weight of essential amino acids in free form and/or salt form.

The term "essential amino acids" (EAA) as used herein, unless otherwise stated, refers to essential amino acids in free form and/or salt form chosen from at least one of isoleucine, leucine, lysine, methionine, phenylalanine, threonine, tryptophan, valine, and histidine. It is to be understood that "leucine" as used herein, unless otherwise stated, refers to leucine in free form and/or salt form.

The term "total leucine" or "total amino acid, e.g. essential or conditionally essential or non-essential amino acid" as used herein refers to leucine or amino acid in free and/or salt form plus leucine or amino acid derived from, or bound in, intact protein.

In a further aspect, there is provided a composition of the invention, wherein total leucine, i.e. the sum of leucine in free and/or salt form plus leucine derived from intact protein, is at least about 10 to about 40%, e.g. at least about 15 to about 35%, e.g. at least about 20 to about 30, e.g. about 21, 22, 23, 24 or 25%, e.g. about 22% by weight based on the weight of total amino acids. Total leucine content of the compositions of the invention may be from about 25 to about 45, e.g. about 30 to about 40%, e.g. about 36% of the total essential amino acids. The compositions of the invention may comprise leucine in free and/or salt form:leucine in form of intact protein in a ratio of about 3:1 to about 1:3, for example in a ratio of about 2:about 1. In one aspect of the invention there is provided a composition of the invention comprising a ratio of total leucine leucine in free and/or salt form of about 3:1 to about 1:3, e.g. about 1.5:1.

In yet a further aspect the present invention provides a composition of the invention, wherein the amount of leucine, e.g. total leucine, is up to three times higher than the highest amount of any other essential amino acid, e.g. total essential amino acid.

The invention also relates to compositions further comprising branched-chain amino acids, e.g. valine, leucine, isoleucine, or mixtures thereof, in free and/or in salt form and/or in form of intact protein, in an amount of about 30 to 60%, e.g. of about 35 to 55%, e.g. about 30 or 35 to 45% by weight based on the weight of amino-nitrogen source, e.g. of total amino acids.

In a further aspect of the invention there is provided a composition of the invention with a reduced amount of tryptophan or hydroxytryptophan in free and/or in salt form and/or in form of intact protein, e.g. about less than 5%, e.g. less than about 3% by weight based on the weight of amino-nitrogen source, e.g. of total amino acids.

The invention also relates to compositions of the invention further comprising threonine in free and/or in salt form and/or in form of intact protein in an amount of about 3 or 5 to about 11% by weight based on the weight of amino-nitrogen source, e.g. of total amino acids.

In a further aspect the invention relates to compositions of the invention further comprising valine in free and/or in salt form and/or in form of intact protein in amount of about 6% to about 16%, e.g. about 8 to about 10% by weight based on the weight of amino-nitrogen source, e.g. based on the weight of total of amino acids.

In a further aspect of the invention the compositions of the invention may further comprise conditionally essential amino acids in free and/or in salt form and/or in form of intact protein chosen from at least one of arginine, glutamine, tyrosine, and cysteine.

In a preferred exemplary embodiment of the present invention, the compositions of the invention comprise arginine in free form and/or salt form, e.g. in an amount of about 5% or 10% to about 40%, e.g. about 15% to about 25%, 30% or 35%, e.g. about 15 to 20% by weight based on the weight of amino-nitrogen source, e.g. of the total essential and conditionally essential amino acids. In one aspect, free arginine constitutes about 5% to about 10%, e.g. about 7% of the total amino acids of the compositions of the invention.

In yet another embodiment of the invention the compositions, e.g. pharmaceutical or nutritional compositions, of the invention may have the following amino acid composition: leucine 20 to 35%, e.g. 30%, isoleucine 3 to 6%, e.g. 3 to 4%, valine 5 to 15%, e.g. 8 to 12%, methionine 0.5 to 7%, e.g. 2 to 5%, phenylalanine 8 to 12, e.g. 9 to 10%, lysine 10 to 14%, e.g. 12 to 13%, threonine 8 to 12%, e.g. 9 to 11%, histidine 8 to 12%, e.g. 8 to 11%, arginine 5 to 15% by weight based on the weight of amino-nitrogen source, e.g. of total amino acids. In a further aspect the compositions of the invention may comprise the following concentration rage of amino acids (% molar base): leucine 20 to 40%, e.g. about 35 to 40%, isoleucine 3 to 10%, e.g. about 7%, valine 5 to 15%, e.g. about 10%, methionine 0.5 to 7%, e.g. about 5%, phenylalanine 5 to 12, e.g. about 5%, lysine 8 to 20%, e.g. about 9%, threonine 6 to 12%, e.g. about 6%, histidine 3 to 8%, e.g. about 3%, tryptophan 0 to 4%, e.g. about 1%, arginine 5 to 15%, e.g. about 13%. The amino acids may be in free and/or in salt form and/or in form of intact protein, e.g. in free form, or predominantly in free form. In particular, the compositions of the invention may comprise arginine, leucine and methionine in free and/or salt form, for example in the amounts of about 5% to about 15% arginine, about 10% to about 30% leucine, and about 0.5% to about 5% methionine by weight based on the weight of amino-nitrogen source, e.g. of total amino acids. In a further aspect the compositions of the invention may comprise arginine:leucine:methionine in free form and/or salt form in a ratio of about 0.1 to about 5:about 0.5 to about 10:about 0.01 to about 1, e.g. in a ratio of about 0.5: about 1:about 0.05.

In a further aspect of the present invention the compositions of the invention may further comprise glutamine, e.g. glutamine peptide, e.g. in an amount of about 4 to 9 g per daily dose.

In yet a further aspect of the present invention, the compositions of the invention further comprise intact protein, e.g. protein chosen from at least one of casein, whey protein, soy protein, collagen or wheat protein, preferably whey protein and/or soy protein and/or casein may be used. For example, the invention provides a composition comprising leucine in free form and/or in salt form and intact protein wherein leucine in free form and/or in salt form is present in an amount of about 10%, 15% or 20% to about 25%, 30% or 35%, e.g. about 15% to about 20%, e.g. about 18% by weight based on the weight of intact protein. The compositions of the invention may comprise intact protein:leucine in free and/or salt form in a ratio of about 10:1 to about 1:10, for example in a ratio of about 5:1 to about 1:5, for example in a ratio of about 5:1. The ratio of total amino acids:total leucine may be from about 3:1 to about 6:1, e.g. about 4 to 5:1.

In one aspect, present inventors have found that particularly high levels of essential and, optionally, conditionally essential amino acids may be provided using compositions comprising a combination of a) essential and, optionally, conditionally essential amino acids in free and/or salt form, and b) intact protein, wherein the ratio of total essential and, optionally, conditionally essential amino acids to total amino acids is from about 0.4 to about 0.95, e.g. about 0.45, 0.5, 0.55 or 0.6 to about 0.7, 0.75, 0.8 or 0.9, e.g. about 0.65.

In one aspect the compositions according to the invention provide a ratio of total essential and, optionally, conditionally essential amino acids versus total non-essential amino acids of about 0.65:about 0.45. In a further aspect the compositions of the invention comprise about 40 to about 95%, e.g. about 45, 50, 55 or 60% to about 70, 75, 80 or 90%, e.g. about 65% by weight of total essential and, optionally, conditionally essential amino acids based on the weight of total amino acids.

In another exemplary embodiment of the present invention, the compositions of the present invention comprise a mixture of essential amino acids solely in free form and/or in salt form, e.g. leucine solely in free form and/or in salt form and at least one essential amino acid solely in free form and/or in salt form.

According to the present invention, the compositions of the invention may be provided in form of dietary means, e.g. supplements, or in the form of a nutritional formulation, e.g. a medical food or beverage product, e.g. in form of a complete meal, part of a meal, as food additive or as powder for dissolution, or in the form of a pharmaceutical formulation, e.g. in form of a tablet, pill, sachet or capsule.

In a further aspect of the invention there is provided a medical food or beverage product, dietary supplement or nutritional or pharmaceutical formulation comprising a composition of the invention.

The compositions of the invention in form of dietary means, e.g. supplements, or pharmaceutical formulations may consist exclusively of the compositions of the invention, and optionally pharmaceutically or nutritionally acceptable carriers.

The compositions of the invention may be in medical food or beverage product form, e.g. in form of a powder for dissolution. The powder may be combined with a liquid, e.g. water, or other liquid, such as milk or fruit juice, e.g. in a ratio of powder to liquid of about 1 to about 5, to obtain a ready-to-consume composition, e.g. ready-to-drink composition or instant drink.

Optionally, the compositions according to the invention may be nutritionally complete, i.e. may include vitamins, minerals, trace elements as well as nitrogen, carbohydrate and fat and/or fatty acid sources so that they may be used as the sole source of nutrition supplying essentially all the required daily amounts of vitamins, minerals, carbohydrates, fat and/or fatty acids, proteins and the like. Accordingly, the compositions of the invention may be provided in the form of a nutritionally balanced complete meal, e.g. suited for oral or tube feeding, e.g. by means of nasogastric, nasoduodenal, esophagostomy, gastrostomy, or jejunostomy tubes, or peripheral or total parenteral nutrition. Preferably the compositions of the invention are for oral administration.

Surprisingly and unexpectedly, the present inventors have found that particularly useful compositions for promotion of muscle protein synthesis or controlling tumor-induced weight loss, such as cachexia, e.g. cancer cachexia, may be obtained by combining the mixture of essential amino acids in free form and/or in salt form, alone or in combination with intact protein, as hereinabove described with n−3 polyunsaturated fatty acids, including, but not limited to α-linolenic acid (LNA), eicosapentaenoic acid (EPA), and docosahexaenoic acid (DHA), either alone or in combination with each other. The effect of such a combination is greater than the effect that can be achieved with either type of combination partner alone, i.e. greater than the effect of a nutritional therapy using only the mixture of essential amino acids in free form and/or in salt, alone or in combination with intact protein, or the n−3 fatty acid(s) as defined herein.

Hence, in one aspect the present invention further pertains to a combination comprising a mixture of essential amino acids in free and/or in salt form, wherein leucine, e.g. total leucine, is at least about 10 to about 40%, e.g. at least about 15 to about 35%, e.g. at least about 20 to about 30, e.g. about 15% to about 25%, e.g. about 22%, by weight based on the weight of amino-nitrogen source, e.g. of total amino acids, and at least one n−3 fatty acid chosen from alpha-linolenic acid, eicosapentaenoic acid, and docosahexaenoic acid, wherein leucine may be present in form of a combination of leucine in free and/or salt form and leucine derived from intact protein and the n−3 fatty acid(s) may be present in free form or in form of an oil or fat, e.g. for promotion of muscle protein synthesis or controlling tumor-induced weight loss, such as cachexia, e.g. cancer cachexia.

Such a combination is preferably a combined preparation or a pharmaceutical or nutritional composition.

Preferably the compositions of the invention may comprise EPA and DHA, e.g. EPA and DHA in a ratio of EPA:DHA of about 2:1 to about 1:2, e.g. about 1.5:1.

In a further aspect of the invention the compositions of the invention may comprise EPA and DHA either alone or in combination, e.g. EPA alone, in an amount of at least about 600 mg to about 2 g, e.g. about 1.5 g to about 1.8 g per serving. When combined, EPA may be present in amount of about 500 mg to about 1.5 g, e.g. about 1 g, and DHA may be present in an amount of about 250 mg to about 1.5 g, e.g. about 500 mg to about 750 mg, e.g. about 650 mg, per serving.

In yet a further aspect of the invention the compositions of the invention may comprise a mixture of n−6, e.g. linoleic acid, and n−3 polyunsaturated fatty acids, e.g. chosen from linolenic acid, EPA and DHA, e.g. in a ratio of n−6:n−3 polyunsaturated fatty acids of about 0.1:1 to about 1:0.1, e.g. about 0.2, 0.5 or 0.8 to about 1, 1.2 or 1.5, e.g. about 1.1:1.

In a further aspect the compositions of the invention may comprise about 2 g or 2.5 to about 3.5 g, e.g. about 2.5 g or 3 g per serving of monounsaturated fatty acids (MUFA) and about 3 g or 3.5 g to about 4 g or 6 g, e.g. about 4.5 g or 5 g per serving of polyunsaturated fatty acids (PUFA).

Nutritional formulations comprising the compositions of the invention, e.g. medical food or beverage product, comprise other nutritional components, e.g. fats and/or carbohydrates, in addition to the mixture of essential amino acids in free and/or in salt form and optionally the n−3 fatty acid(s). Dietary oils may be used in the preparation of the nutritional compositions of the invention. Dietary oils include but are not limited to canola, medium chain triglycerides (MCT), fish, soybean, soy lecithin, corn, safflower, sunflower, high-oleic sunflower, high-oleic safflower, olive, borage, black currant, evening primrose and flaxseed oil. Preferably fish oil may be used, e.g. an oil comprising about 45% EPA and about 10% DHA, e.g. as known and commercially available under the trade name EPAX® 4510 from Pronova Biocare (Lysaker, Norway), or concentrated fish oil, comprising e.g. about 70% EPA.

The dose of dietary oil per serving, e.g. in the form of fish oil, may comprise for example about 0.5 g to about 3 g, e.g. about 1.5 g to about 2 g, of n–3 polyunsaturated fatty acids.

The dose of dietary oil per serving may comprise for example about 2.5 g, 3.5 g or 4.5 g to about 5.5 g, 6.5 g or 7.5 g, e.g. about 5.5 g of fish oil and/or about 0.5 g, 1 g, 1.5 g, 2 g or 2.5 g to about 3 g, 3.5 g, 4 g, 4.5 g or 5 g, e.g. about 1 g to about 3 g, e.g. about 1 g of medium chain triglycerides (MCT).

According to the invention, up to 5 or 6, e.g. about 2 to 3 servings may be given per day.

In a further aspect of the present invention the compositions of the invention, e.g. nutritional compositions, may further comprise soluble fibers, e.g. agar, alginates, carubin, pectin and its derivatives, e.g. pectins from fruits and vegetables, and more preferably pectins from citrus fruits and apple, beta-glucan, such as oat beta-glucan, carrageenans, e.g. kappa, lambda and iota carrageenans, furcellaran, inulin, arabinogalactan, cellulose and its derivatives, scleroglucan, psyllium, such as psyllium seed husk, mucilages and gums. According to the invention, gums and mucilages are preferably plant exudates. In particular, the term "gum" as used herein refers to the commonly available vegetable gums and more particularly to konjac gum, xanthan gum, guar gum (guaran gum), locust bean gum, tara bean gum, gum tragacanth, arabic gum, karaya gum, gum ghatti, gellan gum and other related sterculia gum, alfalfa, clover, fenugreek, tamarind flour. Native and modified, e.g. hydrolyzed, soluble fibers may be used according to the invention. According to the invention, preferably guar gum, e.g. hydrolyzed guar gum, may be used.

The compositions of the invention may further deliver about 5 g to about 15 g per day, e.g. about 9 g per day soluble fiber, for example in the form of inulin and hydrolyzed guar gum, e.g. in 3 servings of about 3 g.

In one embodiment of the present invention the daily delivery of amino-nitrogen source may be from about at least 10 g to about 60 g, e.g. from about 15 g to about 55 g, e.g. about 20 to about 50 g, e.g. about 44 to about 54 g. Optimally at least about 6 g to about 18 g, e.g. about 10 g to about 12 g of the total amino-nitrogen source per daily dose are amino acids in free form and/or in salt form. At least about 3 g up to about 15 g, e.g. about 6 g, 7.5 g, 8 g or 8.5 g to about 12 g, e.g. about 8 g of the total amino-nitrogen source per daily dose are essential amino acids in free form and/or in salt form. The daily dose of e.g. about 15 g essential amino acids, e.g. in free and/or salt form, may be given 3 times per day, e.g. in 3 servings of about 5 g, with equal effectiveness. In one aspect the daily delivery of leucine in free and/or salt form may be from about 5 g to about 10 g, e.g. in an amount of about 8 g. The daily delivery of total leucine may be from about 10 g to about 20 g, e.g. about 12 g to about 15 g, e.g. about 12 g. In one aspect of the invention total essential and, optionally, conditionally essential amino acids may be delivered in an amount of from about 6 to about 21 g per serving, e.g. from about 6 to about 12 g per serving.

The daily delivery of the optional nutrients referred to hereinabove may vary depending on body weight, sex, age and/or medical condition of the individual. All indicated proportions described above are accordingly to be understood as being indicative of preferred or individually inventive teaching only and not limiting the invention in its broadest aspect.

In a further embodiment of the invention, the nutritional product provides at least 100%, e.g. 100%, of the U.S. RDA for vitamins and minerals per daily dose.

The present inventors have found that particularly high amounts of vitamin E are useful in the compositions as hereinabove described for promotion of muscle protein synthesis or controlling tumor-induced weight loss, such as cachexia, e.g. cancer cachexia.

Hence, in a further aspect the invention also pertains to compositions of the invention further comprising tocopherol and/or tocotrienol, e.g. Vitamin E (α-tocopherol), in an amount of about 50 mg to about 400 mg, e.g. about 100 mg or 200 mg to about 300, e.g. about 150, 240 mg or 300 mg per daily dose, e.g. in three servings of about 50 or 100 mg.

The caloric density of the compositions, e.g. nutritional compositions of the invention may be about 1.5 kcal/mL, e.g. about 600 to about 1500 kcal per day, e.g. about 720 to about 900 kcal per day, in the form of about two to about five or six servings per day, e.g. in three servings of about 310 kcal. A suitable serving size may be in the range of about 20 to about 500 ml, preferably about 50 to about 250 ml, e.g. about 200 or 240 ml. The compositions of the invention may provide benefit with as few as for example two servings per day. Levels of amino-nitrogen source, e.g. intact protein or amino acids, e.g. essential amino acids, or fatty acids, or carbohydrate on a per liter basis are not crucial, provided that a reasonable volume supplies the recommended amounts in accordance with the invention. A typical nutritional composition useful according to the invention will have a caloric distribution of about 12 to about 24%, e.g. about 23% from a source of amino nitrogen, e.g. protein, e.g. amino acids in free form and/or in salt form in combination with intact protein, about 40 to about 65%, e.g. about 46% from carbohydrate, for example in the form of maltodextrin and sucrose, and about 10 to about 35%, e.g. about 30% from fat, for example in the form of fish and vegetable oil.

Nutritional compositions in accordance with the present invention may be provided as a medical food or beverage product, e.g. in oral nutritional form, e.g. as a health drink, as a ready-made drink, optionally as a soft drink, including juices, milk-shake, yogurt drink, smoothie or soy-based drink, in a bar, or dispersed in foods of any sort, such as baked products, cereal bars, dairy bars, snack-foods, soups, breakfast cereals, muesli, candies, tabs, cookies, biscuits, crackers (such as a rice crackers), and dairy products.

Preferably the compositions of the invention may be administered as a nutritional formulation, e.g. as part of a meal, e.g. in the form of a health drink, e.g. ready-to-use drink.

Nutritional compositions in accordance with the present invention may be administered in form of a single composition that contains all components, e.g. essential amino acids, fatty acids and/or soluble fibers, or each component may be administered individually. For example a liquid nutritional formulation, e.g. in the form of a syrup, suspension, emulsion or solution, may contain all components except for the essential amino acids, e.g. except for the branched-chain amino acids and/or glutamine, e.g. glutamine peptide, if present. For example, the branched-chain amino acids and/or glutamine, e.g. glutamine peptide, if present, may be administered in form of a solid oral dosage form, e.g. in form of a capsule, pill, tablet, dragées, or sachet.

Solid oral dosage forms are prepared in a manner known per se, for example by means of conventional mixing, granulating, confectioning, dissolving or lyophilizing processes.

For example, compositions for oral administration may be obtained by combining the active ingredients with solid carriers, optionally granulating a resulting mixture and processing the mixture or granules, if desired or necessary after the addition of suitable excipients, to form tablets or dragée cores.

Suitable physiologically acceptable carriers may be especially fillers, such as sugars, for example lactose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, and, if desired, disintegrators, such as the above-mentioned starches, and also carboxymethyl starch, cross-linked polyvinylpyrrolidone, agar, or alginic acid or a salt thereof, such as sodium alginate. In one aspect of the invention the compositions of the invention may be lactose-free. Further excipients may be especially flow-conditioners and lubricants, for example silicic acid, talc, stearic acid or salts thereof, such as magnesium or calcium stearate, and/or polyethylene glycol. Dragée cores are provided with suitable coatings, there being used inter alia concentrated sugar solutions which may contain Arabic gum, talc, polyvinylpyrrolidone, polyethylene glycol and/or titanium dioxide, or coating solutions in suitable organic solvents or solvent mixtures. Dyes or pigments may be added to the tablets or dragée coatings, for example for identification purposes or to indicate different doses of active ingredient.

Other orally administrable compositions may be in the form of hard gelatin capsules or soft, sealed capsules consisting of gelatin and a plasticizer, such as glycerol or sorbitol. The hard gelatin capsules may comprise the composition of the invention in the form of granules, for example in admixture with fillers, such as lactose, binders, such as starches, and/or glidants, such as talc or magnesium stearate, and, if desired, stabilizers. In soft capsules the composition of the invention is preferably dissolved or suspended in suitable liquids, such as fatty oils, paraffin oil or liquid polyethylene glycols, it is likewise being possible to add stabilizers.

Conventional additives may be included in the compositions of the invention, including any of those selected from preservatives, chelating agents, osmotic agents, buffers or agents for pH adjustment, effervescing agents, sweeteners, e.g. artificial sweeteners, flavoring agents, coloring agents, taste masking agents, acidulants, emulsifiers, stabilizers, thickening agents, suspending agents, dispersing or wetting agents, antioxidants, acidulants, texturizers, antifoams, and the like.

In addition to the foregoing the present invention also provides a process for the production of a composition, e.g. nutritional or pharmaceutical formulation, as hereinbefore defined, which process comprises bringing the individual components thereof into intimate admixture and, when required compounding the obtained composition in a food or beverage product, for example ready-made drink, or in unit dosage form, for example filling said composition into gelatin capsules.

In another aspect the present invention provides a method for controlling tumor-induced weight loss, such as cachexia, e.g. cancer cachexia, e.g. treating or preventing or ameliorating the effects of cachexia, e.g. cancer cachexia, and/or anorexia, comprising enterally administering to a human in need of such treatment any composition disclosed herein.

In yet a further aspect the present invention provides for promotion of or stimulating muscle protein synthesis, or ameliorating loss of muscle in a human comprising enterally administering to a human in need of such treatment a composition of the invention.

In yet a further aspect the invention provides a method of preventing catabolism and increasing protein synthesis in a subject undergoing metabolic stress, which comprises administering to a human in need of such treatment a composition of the invention.

The invention further provides a use of the compositions as described herein for the dietary management of malnutrition, e.g. protein-energy malnutrition.

In yet another aspect of the invention there is provided a use of the compositions of the invention in the manufacture of a medicament for the treatment and/or prevention of tumor-induced weight loss, such as cachexia, e.g. cancer cachexia, and/or anorexia, ameliorating the effects of cachexia, e.g. cancer cachexia, and/or anorexia, stimulating muscle protein synthesis, or ameliorating loss of muscle in a human.

The method of treatment or use as claimed herein is applicable to tumor-induced weight loss, such as cancer cachexia, or anorexia in human patients suffering from different cancers, e.g. liver, breast, lung, prostate, gastrointestinal or pancreatic cancer. Cachexia or anorexia may be related to the disease itself or the effects of treatment.

The method of treatment or use according to the invention may be combined with pharmacological and alternative/complementary medicine therapies and/or with educational interventions, e.g. to treat and manage the physical and emotional symptoms associated with cachexia, e.g. cancer cachexia, and/or anorexia. For example, the compositions of the invention may be combined with anti-cancer drugs, such as 5-fluorouracil, mitomycin-C, adriamycin, chloroethyl nitrosureas and methotrexate. In a further aspect the compositions may be combined with interleukin-15.

In a further aspect of the present invention there may be provided a combined pharmaceutical formulation for simultaneous, separate or sequential use for the treatment or prevention of cachexia, e.g. cancer cachexia, and/or anorexia comprising a composition of the invention, and one or more anti-cancer drug(s).

Dependent on the form of application of the compositions of the invention, i.e. as complete meal, part of a meal, food additive, drink, sachet, tablet or capsule, the compositions of the invention may be taken once daily to five or six times daily. For patients using the compositions of the invention as a supplement to a normal diet, the daily dose may be two servings per day. For patients receiving the compositions of the invention as their entire daily nutritional intake, up to six servings per day may be recommended. The compositions of the invention may be served without restriction to time of day, e.g. together with the main meals, preferably between meals.

The compositions of the invention may be administered under the supervision of a medical specialist, or may be self-administered.

For treatment of tumor-induced weight loss, such as cachexia, e.g. cancer cachexia, and/or anorexia under clinical supervision it is possible to combine the nutritional approach with conventional pharmaceutical therapies such as anti-cancer drugs. The anti-cancer drugs may conveniently be formulated together with the compositions of the invention in standard pharmaceutical dosage forms. In a further aspect of the invention the composition of the invention may be provided in form of a kit for separate, sequential or simultaneous administration in conjunction with one or more anti-cancer drug(s).

Optimally, the composition, e.g. nutritional composition or dietary supplement, of the invention is consumed for the duration of patient care and treatment, e.g. until weight is regained or lean body mass is increased. Since these formulations are safe to consume, cachectic or anorectic patients, can continue taking these supplements for as long as required, e.g. until normal weight or lean body mass has been resumed. Early intervention may be a critical success factor for improved outcome in patients with cachexia, e.g. cancer cachexia.

Anyone perceived to be at risk from tumor-induced weight loss, e.g. cachexia and/or anorexia or subjects already suffering from cachexia, e.g. cancer cachexia, and/or anorexia, can benefit from ingesting the compositions of the invention. The compositions of the invention may be particularly indicated for patients with solid tumors with cachexia or at risk of developing it. By stimulating muscle protein anabolism, the compositions of the invention have the potential to reduce the rate of or reverse tumor-induced weight loss, e.g. cachexia, to promote weight gain, stimulate muscle growth, enhance immune function, restore metabolic balance, support increased resistance to infection, improve tolerance to cancer therapy, enhance response to cancer therapy, reduce morbidity, improve associated symptoms that affect quality of life, such as weakness, fatigue, gastrointestinal distress, sleep/wake disturbances, pain, listlessness, shortness of breath, lethargy, depression, malaise.

In accordance with the invention as presently claimed it is possible to effectively ameliorate symptoms and conditions associated with tumor-induced weight loss, e.g. cachexia and/or anorexia with natural compounds, which do not show any severe side effects. Further, the present methods are well-tolerated, for example without causing any discomfort or nausea, and simple to apply.

The utility of all the compositions of the present invention may be observed in standard clinical tests in, for example, indications as described hereinabove, for example using dosages of amino acids in free form and/or in salt form, in the range of about 0.05 to about 0.3 g/kg body weight/day, preferably from about 0.085 to about 0.25 g/kg body weight/day, more preferably from about 0.1 or 0.15 to about 0.2 g/kg body weight/day, or using dosages of total essential amino acids in the range of from about 6 to about 12 g or up to about 21 g per serving, or from about 36 to about 72 g total essential amino acids per day, for a mammal, e.g. adult, and in standard animal models. The effect of the compositions of the invention, on prevention and treatment of tumor-induced weight loss, e.g. cachexia can be monitored by any of the methods known to one skilled in the art, e.g. food intake, body weight, anthropometric measurements, serum levels of lipids, fatty acids, amino acids, levels of serologic markers, serotonin, C-reactive protein, TNF alpha, IL-1, changes in the morphology of tumors.

One human clinical trial may be affected as follows:

A randomized double blind study comparing the compositions of the invention, e.g. using dosages of amino acids in free form and/or in salt form, in the range of about 0.05 to about 0.3 g/kg body weight/day, preferably from about 0.085 to about 0.25 g/kg body weight/day, more preferably from about 0.1 or 0.15 to about 0.2 g/kg body weight/day and dosages of n–3 polyunsaturated fatty acids in the range of about 0.05 to about 0.3 g/kg body weight/day, preferably from about 0.06 to about 0.2 g/kg body weight/day, more preferably from about 0.06 to about 0.13 or 0.15 g/kg body weight/day, or using dosages of total essential amino acids in the range of from about 6 to about 12 g or up to about 21 g per serving, or from about 36 to about 72 g total essential amino acids per day, to a standard nutritional supplement may be performed in patients with advanced pancreatic cancer aiming at comparison of the effect on lean body mass, assessment of the effect on mediators in serum and urine, pro-inflammatory cytokines and muscle metabolism, and assessment of changes in performance status, quality of life and survival. 125 patients per treatment group may be tested, e.g. assessing the following parameters: change in lean body mass between baseline and week 12, body weight, nutritional intake and fatty acid analysis. In addition, for a subgroup of forty patients, baseline versus three weeks investigations may be undertaken for: Urinary Proteolysis Inducing Factor, acute phase protein response (C-reactive protein concentration) and pro-inflammatory cytokines, Ubiquitin metabolism (muscle biopsy in 15 patients) and the acceptability of the product, e.g. taste, and compliance with the treatment regimen.

The invention will now be further illustrated by the following examples.

Example 1

An experiment was performed in healthy older subjects ($\bar{x}=71\pm2$ yr) to determine if non-essential amino acids, i.e. amino acids synthesized within the body at a rate sufficient to provide daily requirements, are needed for an amino acid mixture to stimulate muscle protein synthesis. The response of muscle protein metabolism to either 18 g of essential amino acids (EAAs) or 40 g of balanced amino acids (BAA, EAAs+ 22 g non-essential amino acids) given orally over a three-hour period was compared. Muscle protein metabolism was measured in the basal state and during oral amino acids using L-$^2$H$_5$-phenylalanine infusion, femoral arterial and venous catheterization, and muscle biopsies. The exact mixtures of amino acids tested are shown in Table 1.

TABLE 1

Amino acids content of the two supplements administered to the two groups of older subjects. The supplements were made of crystalline amino acids and dissolved in 540 ml of water containing a sugar-free flavor.

|  | Essential Amino Acids | Balanced Amino Acids |
|---|---|---|
| Alanine (g) | — | 2.4 |
| Arginine (g) | — | 2.8 |
| Asparagine (g) | — | 3.7 |
| Cysteine (g) | — | 0.5 |
| Glutamine (g) | — | 5.8 |
| Glycine (g) | — | 1.8 |
| Histidine (g) | 2.0 | 2.0 |
| Isoleucine (g) | 1.9 | 1.9 |
| Leucine (g) | 3.2 | 3.2 |
| Lysine (g) | 3.9 | 3.9 |
| Methionine (g) | 1.0 | 1.0 |
| Phenylalanine (g) | 1.6 | 1.6 |
| Proline (g) | — | 1.9 |
| Serine (g) | — | 1.6 |
| Threonine (g) | 1.9 | 1.9 |
| Tryptophan (g) | 0.5 | 0.5 |
| Tyrosine (g) | — | 1.4 |
| Valine (g) | 2.2 | 2.2 |
| Total Amino Acids (g) | 18.2 | 40.1 |
| Total Energy (kJ [kcal]) | 309 [74] | 682 [163] |

Results

Net muscle protein synthesis (reflected by phenylalanine kinetics) increased similarly from basal ($p<0.01$) in both groups (BAA: $-16\pm5$ to $16\pm4$; EAA: $-18\pm5$ to $14\pm13$ nmol·$^-$$_1$·100 ml leg$^{-1}$) due to a similar increase ($p<0.01$) in muscle protein synthesis (BAA: $43\pm$ to $67\pm11$; EAA: $62\pm6$ to $75\pm10$ nmol·min$^{-1}$·100 ml leg$^{-1}$) and no change in breakdown.

The results indicate that essential amino acids are solely responsible for the amino acid-induced stimulation of muscle protein anabolism.

Example 2

Figure 1:
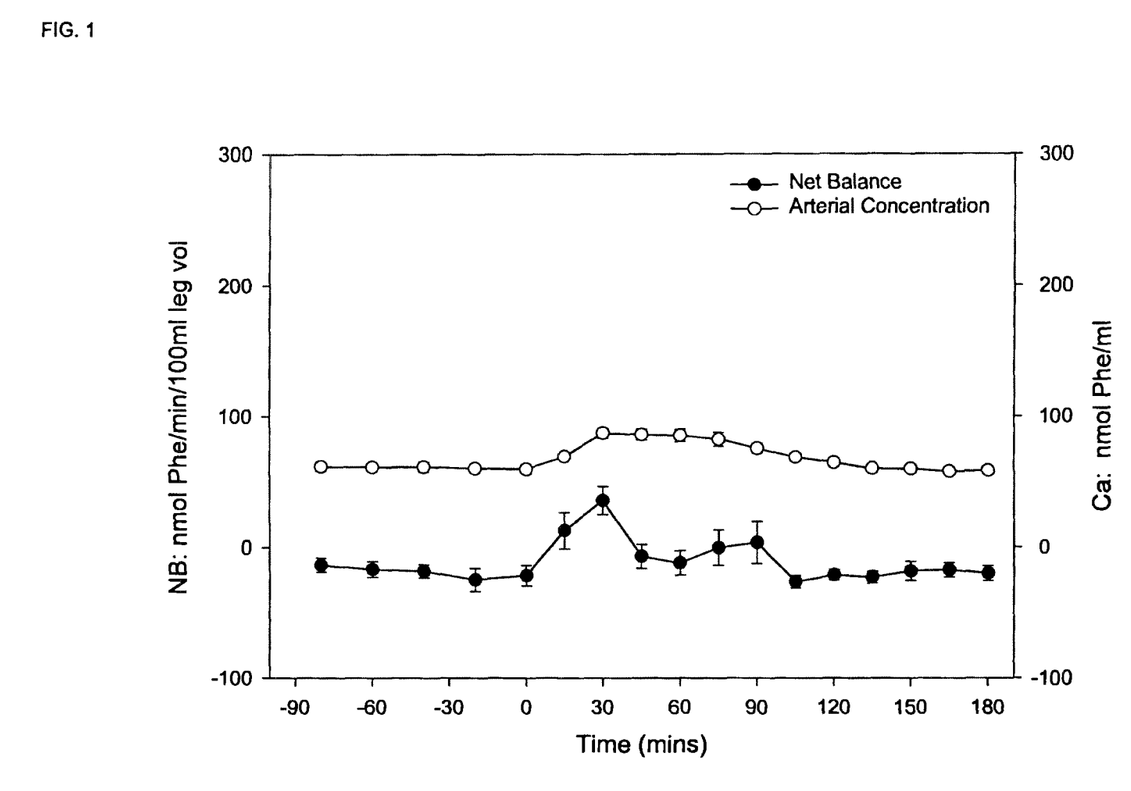
FIG. 1 shows response of plasma phenylalanine concentration and net balance (reflection of net protein synthesis) to ingestion of 15 g of whey protein.
Figure 2:
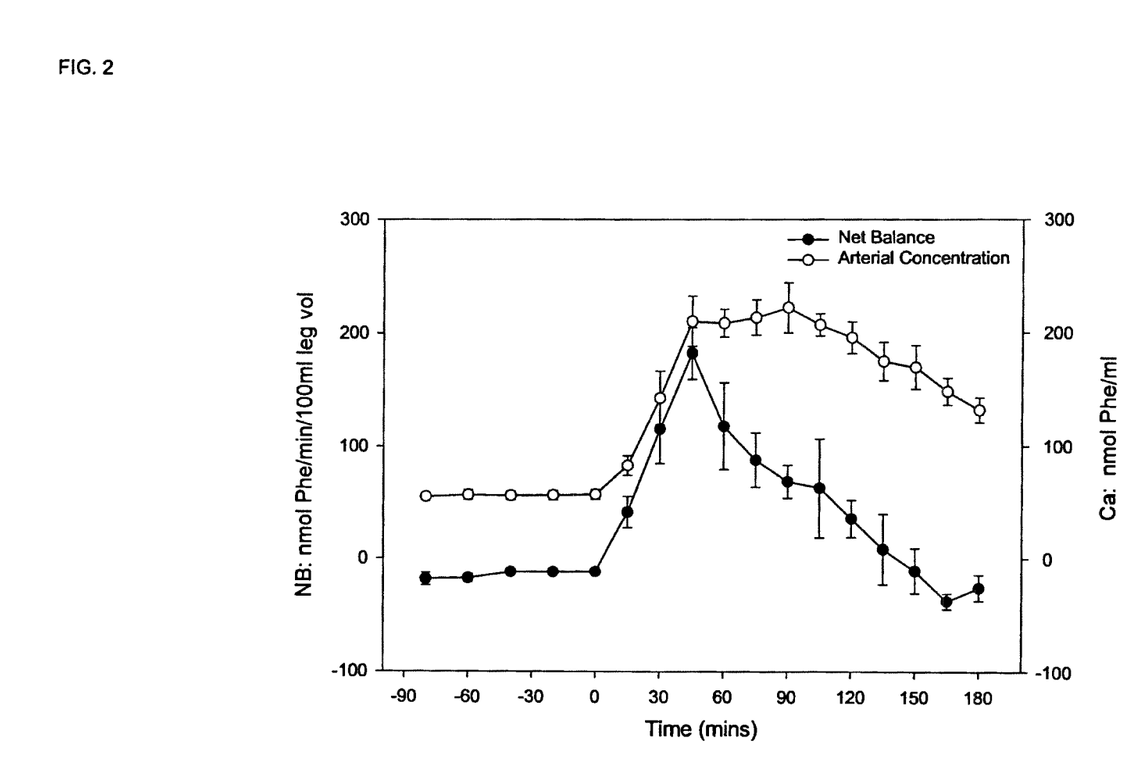
FIG. 2 shows phenylalanine concentration and net balance in response to 15 g of a solution of essential amino acids (EAAs).
Figure 3:
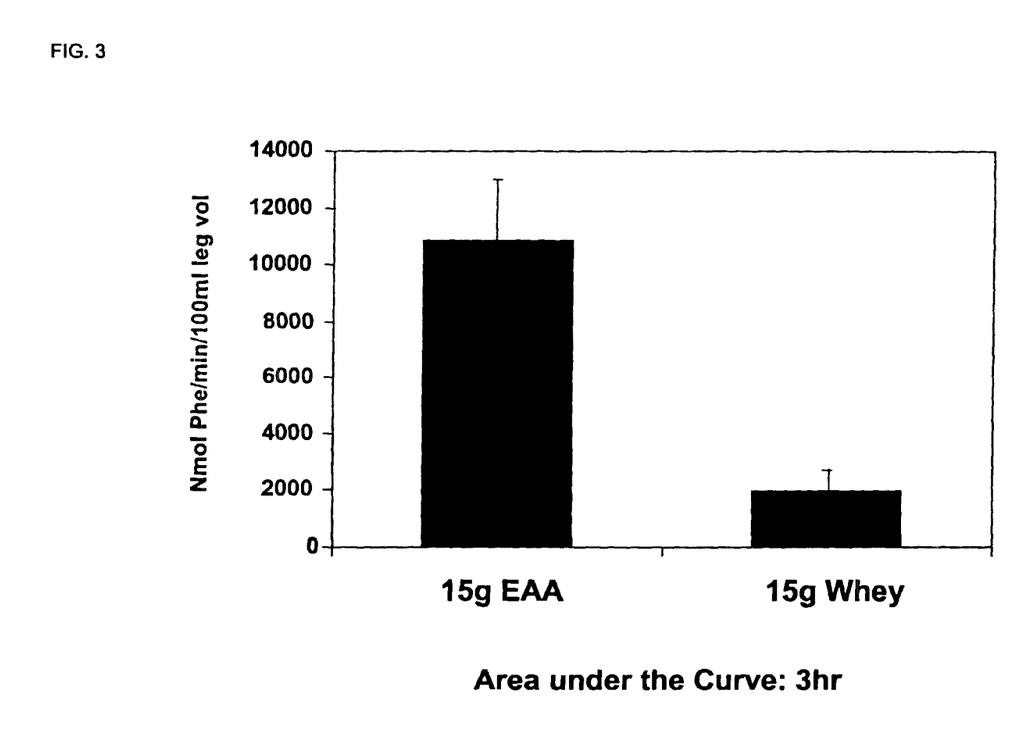
FIG. 3 shows comparison of total response of net muscle protein synthesis to EAAs vs whey protein. Significantly different, $p<0.001$.

The effect of a mixture of free essential amino acids on muscle protein synthesis stimulation was compared with the effect of a same amount of protein. Elderly volunteers (n=5) were given 15 g of free essential amino acids (leucine, isoleucine, methionine, phenylalanine, histidine, lysine, and threonine) on one occasion and 15 g of whey protein on another. The results are shown in FIGS. 1 and 2. Net muscle protein synthesis, i.e. the balance between protein synthesis and breakdown, was measured using the A-V balance technique and stable isotope tracers, as described in Biolo et al, *Am J. Physiol.* 267(39):E467-474, 1994, which is hereby incorporated by reference. Even though whey protein is a rapidly absorbed protein, as compared to other proteins such as casein, the change in plasma phenylalanine concentration (representative of all EAAs) was modest and transient (see, FIG. 1). In contrast, phenylalanine concentration peaked rapidly and at a much higher concentration after ingestion of the free EAAs (see, FIG. 2). The response of net protein synthesis is also shown in FIGS. 1 and 2. The pattern of net balance corresponded to the changes in concentration. The total response to the EAA drink was more than twice that of the intact protein, even though comparable amounts of N were ingested (see, FIG. 3).

The results indicate that ingestion of EAAs is more effective than ingestion of a comparable amount of intact protein in stimulating net muscle protein synthesis in unstressed elderly individuals.

Example 3

To investigate the optimal mixture of free amino acids for stimulating net muscle protein synthesis a series of studies in New Zealand white rabbits weighing about 4.5 kg was performed. Net muscle protein balance was quantified by a technique analogous to the one used for human studies as described in Biolo et al, *J Parent Enteral Nutr* 16:305-315, 1992, which is hereby incorporated by reference, except that leg blood flow was measured by flow probe. This animal model is designed to represent a stress model induced by the surgical procedures needed to collect the samples and therefore is considered to be a good model for a seriously-ill cancer patient. Different amino acid mixtures were infused into the rabbits, and the response of muscle quantified.

The groups were as follows:

Controls: No amino acids

AA group: A balanced AA solution (10% TRAVASOL®) containing all amino acids (27.3 umol·kg$^{-1}$·min$^{-1}$)

EAA group: Only essential amino acids (27.3 umol·kg$^{-1}$·min$^{-1}$)

Leu (25%)+AA group: Leucine was added to the balanced AA solution to account for 25% of total nitrogen and infused at the same total nitrogen group as others (27.3 umol·kg$^{-1}$·min$^{-1}$)

Leu (35%)+AA group: Same as above, except Leu comprised 35% of total

Leu only: Leucine only at 8.3 umol·kg·min

The amino acid composition of each mixture is shown in Table 2.

TABLE 2

Amino acid composition in 100 ml of the infusion solutions.

| | Balanced EAA | Leu (25%) + AA | Leu (35%) + AA | Leu |
|---|---|---|---|---|
| Leu | 730 mg | 1.86 g | 3.63 g | 5.02 g | 4.37 g |
| Ile | 600 mg | 1.01 g | 472 mg | 390 mg | 0 |
| LysHCl | 580 mg | 1.56 g | 456 mg | 377 mg | 0 |
| Val | 580 mg | 1.15 g | 456 mg | 377 mg | 0 |
| Phe | 560 mg | 1.56 g | 441 mg | 287 mg | 0 |
| His | 480 mg | 1.09 g | 378 mg | 312 mg | 0 |
| Thr | 420 mg | 1.47 g | 330 mg | 273 mg | 0 |
| Met | 400 mg | 0.31 g | 315 mg | 260 mg | 0 |
| Trp | 180 mg | 0.11 g | 142 mg | 117 mg | 0 |
| Ala | 2.07 g | | 1.63 g | 1.35 g | 0 |
| Arg | 1.15 g | | 905 mg | 748 mg | 0 |
| Gly | 1.03 g | | 810 mg | 670 mg | 0 |
| Pro | 680 mg | | 535 mg | 442 mg | 0 |
| Ser | 500 mg | | 393 mg | 325 mg | 0 |
| Tyr | 40 mg | | 31 mg | 26 mg | 0 |

Table 3 compares the amount of leucine infused as a function of total N.

TABLE 3

(1) Leucine infusion

| Solution | Leu infused μmol·kg$^{-1}$·min$^{-1}$ | Total N infused μmol·kg$^{-1}$·min$^{-1}$ | % of Leu to total N |
|---|---|---|---|
| TRAVASOL® | 1.39 | 27.3 | 5% |
| EAA | 4.37 | 27.3 | 16% |
| Leu (25%) + AA | 6.93 | 27.3 | 25% |
| Leu (35%) + AA | 9.58 | 27.3 | 35% |
| Leu alone | 8.75 | 8.75 | 100% |

Data are means ± SEM in μmol·kg$^{-1}$·min$^{-1}$.
*p < 0.05 vs. control.
In the EAA group no statistical analysis was done.

The results are shown in Table 4.

TABLE 4

Protein kinetics in muscle

| | Synthesis | Breakdown | Net balance |
|---|---|---|---|
| Control (n = 6) | 5.4 ± 0.6 | 9.2 ± 1.1 | −3.8 ± 0.5 |
| TRAVASOL® (n = 6) | 4.3 ± 0.7 | 8.7 ± 1.0 | −4.4 ± 1.0 |
| EAA (n = 4) | 4.6 ± 1.2 | 9.5 ± 1.7 | −4.9 ± 0.6 |
| Leu (25%) + AA (n = 6) | 6.8 ± 1.1* | 8.1 ± 1.2 | −1.2 ± 0.2* |
| Leu (35%) + AA (n = 8) | 6.9 ± 0.6* | 8.0 ± 0.4 | −1.0 ± 0.4* |
| Leu alone (n = 5) | 6.6 ± 0.7 | 9.2 + 0.5 | −2.6 ± 0.3 |

Data are means ± SEM in μmol·kg$^{-1}$·min$^{-1}$.
*p < 0.05 vs. control.

Neither a balanced solution, nor the EAA solution, stimulated net muscle synthesis at the dosage given. In contrast, when the mixture was enriched with leucine a stimulatory effect on synthesis was observed.

Example 4

Mixtures of EAAs+arginine for nutritional supplement effective in ameliorating loss of muscle in cancer patients. Values are % of total amino acids (molar base).

|   | 4.1 | 4.2 | 4.3 | 4.4 Range |
|---|-----|-----|-----|-----------|
| Leucine | 30 | 30 | 38.8 | 25-40 |
| Isoleucine | 3 | 4 | 7.4 | 3-10 |
| Valine | 9 | 8 | 10.4 | 5-10 |
| Methionine | 3 | 5 | 4.6 | 1-5 |
| Phenylalanine | 10 | 9 | 5.5 | 5-12 |
| Lysine | 13 | 12 | 9.4 | 8-20 |
| Threonine | 9 | 11 | 6.4 | 6-12 |
| Histidine | 8 | 11 | 3.4 | 3-8 |
| Arginine | 15 | 10 | 13.0 | 10-15 |
| Tryptophan | — | — | 1.2 | 1-4 |
|   | 100 | 100 | 100 | 62-115 |

Example 5

A cancer supplement in form of a ready to drink composition.

Example 5A

|   | Percent | Grams/serv. |
|---|---------|-------------|
| Water | 66.6667 | 176.667 |
| Canola oil | 1.8567 | 4.920 |
| MCT oil | 1.0411 | 2.759 |
| EPAX ® 4510 (Marine Oil) | 1.1878 | 3.148 |
| DHA Gold ® (Algae Oil) | 0.3511 | 0.930 |
| Ca caseinate | 6.8900 | 18.259 |
| Partially hydrolyzed guar gum | 1.6978 | 4.499 |
| Arginine | 0.6944 | 1.840 |
| Leucine | 0.5511 | 1.460 |
| Valine | 0.2978 | 0.789 |
| Methionine | 0.0300 | 0.080 |
| Phenylalanine | 0.2456 | 0.651 |
| Sucrose | 7.6089 | 20.164 |
| Corn Syrup (25DE) | 9.4344 | 25.001 |
| Potassium citrate | 0.1889 | 0.501 |
| Sodium citrate | 0.1889 | 0.501 |
| Lactic Acid | 0.0444 | 0.118 |
| Flavor | 0.3989 | 1.057 |
| Sucralose | 0.0700 | 0.186 |
| Sodium chloride | 0.0400 | 0.106 |
| Mono- and Diglycerides | 0.1322 | 0.350 |
| Antifoam | 0.0022 | 0.006 |
| Sodium ascorbate | 0.0300 | 0.080 |
| Vit/Min Premix | 0.3511 | 0.930 |
|   | 100.000 | 265.000 |
| Total (per 100 g) |   |   |
| Total (per serving) |   | 265 Grams |

Example 5B

|   | Grams per Serving | Formula Percent |
|---|-------------------|-----------------|
| Water | 173.95 | 65.6410 |
| MCT oil | 1.2 | 0.4528 |
| Canola oil | 0.6 | 0.2264 |
| Sun oil | 4.5 | 1.6981 |
| EPAX ® 3000TG | 5.7 | 2.1509 |
| Mixed tocopherols | 0.0024 | 0.0009 |
| Ca caseinate | 18.26 | 6.8905 |
| Partially hydrolyzed guar gum | 1.35 | 0.5094 |
| Fructooligosaccharide | 2.3 | 0.8679 |
| Arginine | 1.49 | 0.5623 |
| Leucine | 3.13 | 1.1811 |
| Methionine | 0.18 | 0.0679 |
| Sucrose | 9 | 3.3962 |
| 25DE corn syrup | 38 | 14.3395 |
| Potassium citrate | 0.5 | 0.1887 |
| Sodium citrate | 0.5 | 0.1887 |
| Lactic acid | 1.25 | 0.4717 |
| Flavor | 0.8 | 0.3019 |
| Flavor | 0.4 | 0.1509 |
| Sucralose | 0.132 | 0.0498 |
| Salt | 0.2 | 0.0755 |
| Monos and Diglycerides | 0.490 | 0.1849 |
| Lecithin | 0.133 | 0.0502 |
| Antifoam | 0.0045 | 0.0017 |
| Sodium ascorbate | 0.08 | 0.0302 |
| Vit/Min Premix | 0.85 | 0.3208 |
|   | 265.0019 | 100.000 |

Method: Water is heated to 160° F. and all ingredients except for EPAX® 4510, DHA GOLD®, flavor, sucralose, sodium chloride, sodium ascorbate and lactic acid are added. The mixture is cooled to less than 100° F. and the pH adjusted to 6.5 with lactic acid. The mixture is heated to 140° F. under agitation and after five minutes holding time homogenized at 2500 psi. The remaining ingredients are added and the mixture preheated to 150° F., heated at 290° F. for sec and homogenized at 2500 psi.

For example, the vitamin/mineral pre-mix may comprise the following:

| Maltodextrin powder DE | 37.404155 |
|---|---|
| Dipotassium phosphate | 35.701500 |
| Magnesium oxide | 8.330400 |
| Vitamin E acetate | 7.168900 |
| Tricalcium phosphate | 4.760200 |
| Ferrous sulfate | 1.387600 |
| Zinc sulfate | 1.042500 |
| Biotin, 1% trituration | 0.933000 |
| Niacinamide ($B_3$) | 0.761600 |
| Vitamin A palmitate | 0.606900 |
| Calcium pantothenate | 0.430800 |
| Copper gluconate | 0.380800 |
| Vitamin K | 0.297500 |
| Cyanocobalamin ($B_{12}$) | 0.202300 |
| Manganese sulfate (monohydrate) | 0.172860 |
| Vitamin $D_3$ | 0.119000 |
| Pyridoxine hydrochloride ($B_6$) | 0.095200 |
| Potassium iodide 10% | 0.055258 |
| Thiamine hydrochloride ($B_1$) | 0.054700 |
| Riboflavin ($B_2$) | 0.054700 |
| Chromic acetate (monohydrate) | 0.015480 |
| Folic acid | 0.015333 |
| Sodium molybdate (dihydrate) | 0.005160 |
| Sodium selenite (anhydrous) | 0.004154 |
| Total | 100.000000 |

The individual components can be sourced from the following sources.

Canola oil is from Columbus Foods (Chicago, Ill.).
MCT oil is from Stepan Company (Northfield, Ill.).
EPAX® 4510 (Marine oil) is from Pronova Biocare (Lysaker, Norway)
DHA GOLD® (Algae oil) is from Martek Biosciences Corporation (Columbia, Md.)
Calcium caseinate is from New Zealand Milk Products (Weston, Fla.)

Hydrolyzed guar gum is from Novartis Nutrition Corporation (Minneapolis, Minn.)

Arginine, Leucine, Valine, Methionine, Phenylalanine, are from Ajinomoto (Raleigh, N.C.)

25 DE corn syrup is from Cargill, Inc. (Minneapolis, Minn.)

Vit/min Premix is from Fortitech Inc. (Schenectady, N.Y.)

Mono- and diglycerides are from American Ingredients Inc. (Anaheim, Calif.)

Antifoam is from Dow Corning Corp. (Midland, Mich.)

Example 6

A cancer supplement in form of a ready to drink composition. The composition is prepared according to the method described in Example 5.

|  |  | G/100 ml |
|---|---|---|
| Water |  | 72.7655747 |
| Protein | Na-caseinate | 5.2320000 |
|  | Ca-Caseinate | 2.3980000 |
|  | L-Leucine | 1.3050003 |
|  | L-Arginine | 0.6199996 |
|  | L-Methionine | 0.0752100 |
| Fat | Fish oil | 2.8002100 |
|  | Sunflower oil | 2.0100003 |
|  | MCT oil | 0.5003100 |
| Carbohydrate | Inulin | 1.1172500 |
|  | Sucrose | 1.0900000 |
|  | Maltodextrin | 16.5445530 |
|  | Fructose | 0.5450000 |
|  | Partially hydrolyzed guar gum | 0.5253800 |
| Vitamin E (α-tocopherol) |  | 0.0763000 |
| Vitamins/Minerals |  | 0.2235515 |
| Flavor |  | 0.7517000 |
| Stabilizer |  | 0.0893778 |
| Sweetener |  | 0.0654000 |
| K2H-citrate |  | 0.1962000 |
| K-citrate |  | 0.0599500 |

Equivalent compositions may be obtained employing 0.0327 g Vitamin E per 100 ml.

The examples illustrate compositions useful for example to provide sources of amino acids to counteract protein-energy malnutrition, to optimize protein synthesis and muscle building capacity, help restore and maintain muscle mass and weight, support a potentially improved response to cancer treatment and improve quality of life, on administration of for example from one to six servings of 200 ml per day.

It is understood that while the present invention has been described in conjunction with the detailed description thereof that the foregoing description is intended to illustrate and not limit the scope of the invention, which is defined by the scope of the following claims. Other aspects, advantages and modifications are within the scope of the claims.

The invention is claimed as follows:

1. A composition comprising: leucine, valine in an amount of about 8% to about 10% by weight based on the weight of total amino acids, and at least one essential amino acid in an amount of at least about 15 g in free form per dose, the essential amino acid selected from the group consisting of isoleucine, lysine, methionine, phenylalanine, threonine, tryptophan, histidine, and combinations thereof in free form, the leucine, in free form, being present in an amount of at least 30% to about 95% by weight based on the weight of total amino acids and a ratio of total essential amino acids to total amino acids ranging from about 0.60 to about 0.90.

2. A composition comprising: leucine, valine in an amount of about 8% to about 10% by weight based on the weight of total amino acids, and at least one essential amino acid in an amount of at least about 15 g in free form per dose, the essential amino acid selected from the group consisting of isoleucine, lysine, methionine, phenylalanine, threonine, tryptophan, histidine, and combinations thereof in free form, total leucine being present in an amount of at least 30% to about 35% by weight based on the weight of total amino acids and a ratio of total essential amino acids to total amino acids ranging from about 0.60 to about 0.90.

3. A composition comprising:
   a) leucine, valine in an amount of about 8% to about 10% by weight based on the weight of total amino acids, and at least one essential amino acid in an amount of at least about 15 g in free form per dose, the essential amino acid selected from the group consisting of isoleucine, lysine, methionine, phenylalanine, threonine, tryptophan, histidine, and combinations thereof and, optionally, at least one conditionally essential amino acid selected from the group consisting of tyrosine, cysteine, arginine, glutamine, and combinations thereof in free form, and
   b) at least one intact protein selected from the group consisting of casein, whey protein, soy protein, collagen, wheat protein, and combinations thereof, a ratio of total essential amino acids and, optionally, conditionally essential amino acids to total amino acids ranging from about 0.60 to about 0.90 and the leucine, in free form, being present in an amount of at least 30% by weight based on the weight of intact protein, and the ratio of leucine in free form to leucine in form of the intact protein being about 3:1 to about 1:3.

4. The composition of claim 3, wherein the essential amino acid is at least two selected from the group consisting of isoleucine, lysine, methionine, phenylalanine, threonine, tryptophan, or histidine.

5. The composition of claim 3, further comprising methionine in free form in an amount of at least about 0.5% to about 5% by weight based on the weight of total amino acids.

6. The composition of claim 3, further comprising an n–3 polyunsaturated fatty acid.

7. The composition of claim 6, wherein the n–3 polyunsaturated fatty acid is selected from the group consisting of u-linolenic acid, eicosapentaenoic acid, docosahexaenoic acid, and combinations thereof.

8. The composition of claim 3, further comprising at least about 1 g of eicosapentaenoic acid per serving or at least about 2 g of eicosapentaenoic acid per dose.

9. The composition of claim 3, further comprising tocopherol.

10. The composition of claim 9, wherein the tocopherol is present in an amount about 50 mg per serving or at least 150 mg per dose.

11. The composition of claim 3, comprising from about 15 g to about 55 g of the essential amino acids in free form per dose.

12. The composition of claim 3, comprising from about 12 g to about 15 g leucine in free form per dose.

13. The composition of claim 3, further comprising methionine in free form in an amount of at least about 5% to about 7% by weight based on the weight of total amino acids.

14. A kit comprising:
   a) a first composition comprising:
   1) leucine, valine in an amount of about 8% to about 10% by weight based on the weight of total amino acids, and at least one essential amino acid in an amount of at least about 15 g in free form per dose, the essential amino acid selected from the group consisting of isoleucine, lysine, methionine, phenylalanine, threonine, tryptophan, histidine, and combinations thereof and, optionally, at least one conditionally essential amino acid selected from the group consisting of tyrosine, cysteine, arginine and glutamine in free form, and 2) at least one intact protein selected from the group consisting of casein, whey protein, soy protein, collagen, wheat protein, and combinations thereof, a ratio of total essential amino acids and, optionally, conditionally essential amino acids to total amino acids ranging from about 0.60 to about 0.90 and the leucine, in free form, being present in an amount of at least 30% by weight based on the weight of intact protein, and the ratio of leucine in free form to leucine in form of the intact protein being about 3:1 to about 1:3; and b) a second composition comprising an anti-cancer drug, the anticancer drug being selected from the group consisting of 5-fluorouracil, mitomycin-C, adriamycin, chloroethyl nitrosureas, methotrexate, and combinations thereof.

15. A composition consisting essentially of: leucine, valine in an amount of about 8% to about 10% by weight based on the weight of total amino acids, and at least one essential amino acid in an amount of at least about 15 g in free form per dose, the essential amino acid selected from the group consisting of isoleucine, lysine, methionine, phenylalanine, threonine, tryptophan, histidine, and combinations thereof in free form, and leucine, in free form, being present in an amount of at least 30% by weight based on the weight of total amino acids.

16. A composition consisting essentially of: leucine, valine in an amount of about 8% to about 10% by weight based on the weight of total amino acids, and at least one essential amino acid in an amount of at least about 15 g in free form per dose, the essential amino acid selected from the group consisting of isoleucine, lysine, methionine, phenylalanine, threonine, tryptophan, histidine, and combinations thereof in free form, and total leucine being present in an amount of at least 30% by weight based on the weight of total amino acids.

17. A composition consisting essentially of:
a) leucine, valine in an amount of about 8% to about 10% by weight based on the weight of total amino acids, and at least one essential amino acid in an amount of at least about 15 g in free form per dose, the essential amino acid selected from the group consisting of isoleucine, lysine, methionine, phenylalanine, threonine, tryptophan, histidine, and combinations thereof and, optionally, at least one conditionally essential amino acid selected from the group consisting of tyrosine, cysteine, arginine, glutamine, and combinations thereof in free form, and the leucine, in free form, being present in an amount of at least 30%, and b) at least one intact protein selected from the group consisting of casein, whey protein, soy protein, collagen, wheat protein, and combinations thereof, a ratio of total essential amino acids and, optionally, conditionally essential amino acids, to total amino acids ranging from about 0.60 to about 0.90, and the ratio of leucine in free form to leucine in form of the intact protein being about 3:1 to about 1:3.

18. A kit comprising:
a) a first composition consisting essentially of:
1) leucine, valine in an amount of about 8% to about 10% by weight based on the weight of total amino acids, and at least one essential amino acid in an amount of at least about 15 g in free form per dose, the essential amino acid selected from the group consisting of isoleucine, lysine, methionine, phenylalanine, threonine, tryptophan, histidine, and combinations thereof, and, optionally, at least one conditionally essential amino acid selected from the group consisting of tyrosine, cysteine, arginine, glutamine, and combinations thereof, in free form, and the leucine, in free form, being present in an amount of at least 30%, and 2) at least one intact protein selected from the group consisting of casein, whey protein, soy protein, collagen, wheat protein, and combinations thereof, a ratio of total essential amino acids and, optionally, conditionally essential amino acids to total amino acids ranging from about 0.60 to about 0.90, and the ratio of leucine in free form to leucine in form of the intact protein being about 3:1 to about 1:3; and b) a second composition comprising an anti-cancer drug, the anticancer drug being selected from the group consisting of 5-fluorouracil, mitomycin-C, adriamycin, chloroethyl nitrosureas, methotrexate, and combinations thereof.

* * * * *